United States Patent [19]

Peeters et al.

[11] Patent Number: 4,534,910

[45] Date of Patent: Aug. 13, 1985

[54] METHOD OF PREPARING ACETALS AND ENOL ETHERS FROM ACYLOXYMETHYLENE COMPOUNDS

[75] Inventors: Hermann Peeters, Niederkassel; Wilhelm Vogt, Cologne; Christoph Theis, Bornheim, all of Fed. Rep. of Germany

[73] Assignee: Dynamit Nobel Aktiengesellschaft, Cologne, Fed. Rep. of Germany

[21] Appl. No.: 480,153

[22] Filed: Mar. 29, 1983

[30] Foreign Application Priority Data

Mar. 30, 1982 [DE] Fed. Rep. of Germany ....... 3211679

[51] Int. Cl.$^3$ .................... C07C 121/34; C07C 69/76
[52] U.S. Cl. .................................. 260/465.6; 560/55; 549/491
[58] Field of Search ............ 260/465.8 R, 465.6; 560/55

[56] References Cited

U.S. PATENT DOCUMENTS

| 2,853,510 | 9/1958 | Montagna et al. | 260/465.6 |
| 3,150,142 | 9/1964 | Eby | 260/465.1 |
| 3,324,164 | 6/1967 | Merkel et al. | 260/464 |
| 4,231,956 | 11/1980 | Sullivan, III et al. | 260/465.8 R |
| 4,271,089 | 6/1981 | Butte, Jr. et al. | 260/465.8 R |

OTHER PUBLICATIONS

Chem. Abstracts 75: 140212u, (1971).

*Primary Examiner*—Ethel G. Love
*Attorney, Agent, or Firm*—Felfe & Lynch

[57] ABSTRACT

Enol ethers of the formula

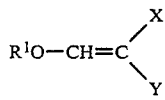

and/or the corresponding acetals can be obtained from acyloxymethylene compounds of the corresponding structure by reaction with the corresponding alcohol, in the presence of acid catalysts if desired.

15 Claims, No Drawings

METHOD OF PREPARING ACETALS AND ENOL ETHERS FROM ACYLOXYMETHYLENE COMPOUNDS

BACKGROUND OF THE INVENTION

The present invention relates to a method for preparing enol ethers and/or acetals.

The preparation of enol ethers of the structure of Formula I is known, but these methods have deficiencies. For example, in accordance with European patent application 0018473, 3-ethoxyacrylonitrile and 3,3-diethoxypropionitrile are obtained only in company with the undesired and difficult-to-separate 3-ethoxy-2-ethylacrylonitrile and 2-(diethoxymethyl)-butyronitrile, respectively. Other methods set out from expensive starting materials, or they are very complicated.

The problem therefore existed of obtaining enol ethers and/or acetals from easily available starting substances, in a smoothly running reaction, and in the highest possible purity.

THE INVENTION

The inventive method provides enol ethers of the formula

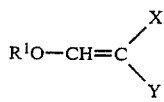

and/or the corresponding acetals from acyloxymethylene compounds of the corresponding structure by reaction with the corresponding alcohol. In addition, the use of acid catalysts is preferred.

In the preferred embodiment, enol ethers of the formula

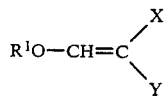   I and/or acetals of the formulas

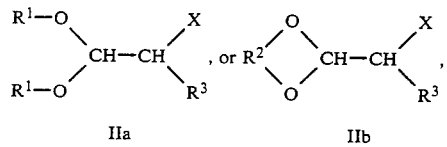

IIa                IIb wherein $R^1$ represents straight-chain or branched alkyl moieties of 1 to 20 carbon atoms or $(CH_2)_m$—Cyc with Cyc=isocyclic or heterocyclic, mononuclear or polynuclear aromatic or cycloaliphatic ring systems bearing in some cases substituents on the rings, with m=0 to 5, the moieties $(CH_2)_nOR^4$ or $(CH_2$—$CH_2O)_nOR^4$ with n=1 to 4 and with $R^4$=straight-chain or branched alkyl moieties of 1 to 12 carbon atoms, $R^2$ represents a double-bonded alkylene or alkenylene moiety of 2 to 6 carbon atoms interrupted in some cases by one or more heteroatoms,
$R^3$=H, straight-chain or branched alkyl moieties of 1 to 20 carbon atoms, straight-chain or branched moieties $(CH_2)_n$—Cn, $(CH_2)_nCOOR^4$, $(CH_2)_nNR^5_2$, $(CH_2)_mOR^4$ or $(CH_2)_mCyc$, n, m, $R^4$ and Cyc having the same meaning as above and $R^5$ alike or unalike H, straight-chain or branched alkyl moieties of 1 to 12 carbon atoms, Cyc or $COR^6$ and $R^6$=H, straight-chain or branched alkyl moieties of 1 to 12 carbon atoms or Cyc,
X represents CN or $COOR^1$ and
Y represents $R^3$ or X,
are prepared by reacting an acyloxymethylene compound of the formula

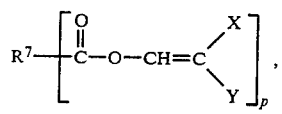   III wherein X and Y have the meaning given above and $R^7$ represents straight-chain or branched alkyl, alkylene, alkenyl or alkenylene moieties of 1 to 12 carbon atoms, isocyclic or heterocyclic ring systems with monocyclic or polycyclic structure or $(CH_2)_nCyc$, wherein n and Cyc have the meaning given above, and p=1 or 2, with an alcohol of the formula

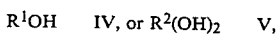

$R^1OH$   IV, or $R^2(OH)_2$   V, wherein $R^1$ and $R^2$ have the meaning given above.

The acyloxymethylene compounds II, which are the starting substances, can easily be obtained by acylation of the hydroxymethylene derivatives of nitriles or of their alkali or alkaline earth salts in accordance with the above-mentioned European patent application, or by the corresponding acylation of hydroxymethylene derivatives of acetic acid ester, aliphatic carboxylic acid ester, alpha-cyanoacetic acid esters, malononitriles or malonic acid esters or their alkali or alkaline earth salts. The moiety $R^7$, when p=1, is the moiety, free of the acyl group, of an aliphatic, cycloaliphatic or heterocyclic, saturated or unsaturated monocarboxylic acid or, when p=2, the moiety, free of both acyl groups, of a saturated or unsaturated, aliphatic, cycloaliphatic or heterocyclic dicarboxylic acid. Preferred acyl groups are the acetyl group and the benzoyl group. As moieties $R^1$ are preferred alkyl groups of 1 to 6 carbon atoms and residues of methyl glycol. As moiety $R^2$ the residue of ethylen glycol is preferred. Other moieties $R^1$ or $R^2$ are preferred whenever the moiety in question is needed in the product. If cyclic ring systems Cyc are involved, the mononuclear ring systems are preferred, followed in preference by the bicyclic.

In the polynuclear ring systems, the rings can be attached to one another directly by one or more atoms or through one or more carbon atoms or hetero atoms as bridges.

The heterocyclic moieties contain preferably nitrogen, in some cases oxygen, or other hetero atoms. Any substituents of the ring systems that may be present can be as desired, provided they are inert in the reaction. Preferred are low alkyl groups of 1 to 3 carbon atoms, chlorine, methoxy, ethoxy or carbalkoxy groups.

For the performance of the process of the invention, the procedure is to react the acyloxymethylene compound together with the alcohol at the reaction temperature, in the presence of a catalyst if desired, and after the end of the reaction to isolate the enol ether and/or the acetal by conventional methods such as distillation or crystallization.

The reactants can be combined together in any desired order. The molar ratio of acyloxymethylene compound to alcohol is from 1:1 to 1:30, preferably 1:2 to 1:15. The alcohols can be particularly alkyl alcohols of 1 to 4 carbon atoms, such as methanol, ethanol, propanol or butanol, but also bivalent alcohols $R^2(OH)_2$, such as for example ethylene glycol, or ether alcohols such as methyl glycol for example. The preferred hetero atoms in diols are nitrogen or oxygen, and in some cases sulfur.

The reaction can take place in the absence, or preferably in the presence, of a catalyst. The catalyst generally produces higher yields and rates of reaction. The catalysts can be proton acids or Lewis acids; the following are given as examples: $HCl$, $H_2SO_4$, $KHSO_4$, $HNO_3$, $H_3PO_4$, $NH_4Cl$, p-toluenesulfonic acid, $FeCl_3$, $AlCl_3$, $ZnCl_2$, $BF_3$, and acid cation exchangers, although this enumeration is not restrictive. The catalyst is used in amounts from 0.01 to 100 mol-%, preferably 0.01 to 40 mol-%, preferably 0.05 to 20 mol-%, referred to the amount of acyloxy methyl compound.

The reaction temperature is from 20 to 250, preferably 50 to 150, degrees Celsius. The reaction generally is performed with refluxing of the alcohol. The pressure is preferably standard pressure, but elevated pressure up to 40 bar is possible. The reaction time amounts generally to from 0.2 to 5, preferably 0.2 to 3 hours.

Separation of the product is generally performed by separating or neutralizing the catalyst or separating its salt and distilling out the excess alcohol, and obtaining the enol ether and/or the acetal in pure form by distillation or crystallization. The neutralization of the catalyst can be performed with bases such as, for example, ammonia, alkali alcoholate, alkali or alkaline earth hydroxides or oxides.

The reaction of the acyloxymethylene compound III with alcohols produces the enol ether or the acetal or mixtures thereof, depending on the nature of the substituent Y, on the reaction conditions and on the product recovery method.

Acyloxymethylene compounds of Formula III in which Y represents only CN or $COOR^1$ react with alcohols to form exclusively the enol ethers of Formula I.

Acyloxymethylene compounds of Formula III with Y representing $R^3$ react to form the enol ethers I or the acetals IIa or IIb or mixtures of the latter with enol ethers I, depending on the conditions of the reaction and of the separation of the product. To provide a slight excess of alcohol, or to leave the catalyst in the reaction mixture while working it up, and the use of high temperatures in the distillation, are helpful in the formation of the enol ether. In the case of the diols $R^2(OH)_2$, acetals of Formula IIb are formed.

The enol ethers and acetals that can be prepared by the method of the invention are intermediates, for examples for the preparation of pharmaceutical products.

EXAMPLES

The following examples will serve for the further explanation of the invention. The examples are to be found in table form.

General Procedure

The alcohol, the catalyst and, as the final component, the acyloxymethylene compound, are combined together and made to react at the reaction temperature given. After separation or neutralization of the catalyst or separation of its salt, if performed, the excess alcohol is distilled out and lastly the enol ether and/or acetal is purified by distillation. The characterization of the product was performed by proton resonance analysis, infrared spectroscopy and mass spectrometry.

Examples

| No. | Acyloxymethylene Compound | Alcohol | Catalyst | Temp. (°C.) | Time (h) | Work-Up | Product | Yield % |
|---|---|---|---|---|---|---|---|---|
| 1. | $CH_3-\underset{\underset{O}{\parallel}}{C}-O-CH=CH-CN$<br>10,8 g<br>0,1 mol | $CH_3OH$<br>32 g<br>1 mol | $AlCl_3$<br>2,7 g<br>0,02 mol | 65 | 2 | with $NaOCH_3$ pH 7, separation of salt | $(CH_3O)_2CH-CH_2-CN$<br>9,0 g | 78,2 |
| 2. | $CH_3-\underset{\underset{O}{\parallel}}{C}-O-CH=CH-CN$<br>10,8 g<br>0,1 mol | $C_2H_5OH$<br>46 g<br>1 mol | HCl<br>0,073 g<br>0,002 mol | 78 | 2 | — | $(C_2H_5O)_2CH-CH_2-CN$<br>12,6 g | 88,0 |
| 3. | $CH_3-\underset{\underset{O}{\parallel}}{C}-O-CH=CH-CN$<br>10,8 g<br>0,1 mol | $\underset{H_3C}{\overset{H_3C}{>}}CH-OH$<br>60 g<br>1 mol | HCl<br>0,2 g<br>0,005 mol | 82 | 3 | — | $\left\{\underset{H_3C}{\overset{H_3C}{>}}\underset{\underset{CHO}{}}{CH}\right\}_2 CH-CH_2-CN$<br>12,2 g | 71,3 |
| 4. | $CH_3-\underset{\underset{O}{\parallel}}{C}-O-CH=CH-CN$<br>10,8 g<br>0,1 mol | $n-C_4H_9OH$<br>74 g<br>1 mol | p-Toluenesulfonic acid<br>1,7 g<br>0,01 mol | 117 | 1 | with sodium butylate pH 7, | $(n-C_4H_9O)_2CH-CH_2-CN$<br>16,9 g | 84,8 |
| 5. | $CH_3-\underset{\underset{O}{\parallel}}{C}-O-CH=CH-CN$<br>10,8 g<br>0,1 mol | $CH_3O-CH_2$<br>   $\vert$<br>$OH-CH_2$<br>76 g<br>1 mol | $H_2SO_4$<br>0,1 g<br>0,001 mol | 123 | 1 | — | $CH_3O-CH_2O-CH=CH-CN$ | 81,4 |
| 6. | $CH_3-\underset{\underset{O}{\parallel}}{C}-O-CH=CH-CN$<br>10,8 g<br>0,1 mol | $HO-CH_2$<br>   $\vert$<br>$HO-CH_2$<br>62,1 g<br>1 mol | $NH_4Cl$<br>1,0 g<br>0,02 mol | 150 | 3 | — | $\begin{array}{c}CH_2-O\\ \vert \qquad \,\,\backslash\\ \qquad\quad CH-CH_2-CN\\ \vert \qquad \,\,/\\ CH_2-O\end{array}$<br>6,2 g | 54,9 |
| 7. | $CH_3-\underset{\underset{O}{\parallel}}{C}-O-CH=CH-COOCH_3$<br>28,8 g<br>0,2 mol | $CH_3OH$<br>48 g<br>1,5 mol | HCl<br>0,037 g<br>0,001 mol | 65 | 1 | with $NaOCH_3$ pH 7, | $(CH_3O)_2CH-CH_2-COOCH_3$<br>21,7 g | 73,3 |

| No. | Acyloxymethylene Compound | Alcohol | Catalyst | Temp. (°C.) | Time (h) | Work-Up | Product | Yield % |
|---|---|---|---|---|---|---|---|---|
| 8. | $CH_3-\overset{O}{\underset{\|}{C}}-O-CH=CH-COOC_2H_5$<br>79,1 g<br>0,5 mol | $C_2H_5OH$<br>230 g<br>5 mol | $KHSO_4$<br>0,68 g<br>0,005 mol | 78 | 3 | with $NaOC_2H_5$ pH 7 | $(C_2H_5O)_2-CH-CH_2-\overset{O}{\underset{\|}{C}}=O$<br>$\phantom{(C_2H_5O)_2-CH-CH_2-C}\overset{\|}{O}$<br>$\phantom{(C_2H_5O)_2-CH-CH_2-C-O}C_2H_5$<br>80,4 g | 84,5 |
| 9. | $CH_3-\overset{O}{\underset{\|}{C}}-O-CH=CH-COOC_2H_5$<br>79,1 g<br>0,5 mol | $C_2H_5-OH$<br>230 g<br>5 mol | $KHSO_4$<br>0,68 g<br>0,005 mol | 78 | 3 | ethanol distilled out 1 hour at 160° C. (760 Torr) Vacuum Distillation | $C_2H_5O-CH=CH-COOC_2H_5$<br>49,0 g | 68,0 |
| 10. | $CH_3-\overset{O}{\underset{\|}{C}}-O-CH=C(COOCH_3)_2$<br>20,2 g<br>0,1 mol | $CH_3OH$<br>32 g<br>1 mol | HCl<br>0,073 g<br>0,002 mol | 65 | 1 | — | $CH_3O-CH=C(COOCH_3)_2$<br>13,9 g | 79,8 |
| 11. | $C_6H_5-\overset{O}{\underset{\|}{C}}-O-CH=C(COOCH_3)_2$<br>0,1 mol | $CH_3OH$<br>32 g<br>1 mol | HCl<br>0,036 g<br>0,001 mol | 65 | 1 | — | $CH_3O-CH=C(COOCH_3)_2$<br>15,0 g | 86,1 |
| 12. | $O=C-O-CH=C(COOCH_3)_2$<br>$\phantom{O=C-O-CH=C}\bigcirc$<br>$O=C-O-CH=C(COOCH_3)_2$<br>33,8 g<br>0,075 mol | $CH_3OH$<br>48 g<br>1,5 mol | HCl<br>0,27 g<br>0,0075 mol | 65 | 2 | — | $CH_3O-CH=C(COOCH_3)_2$<br>19,3 g | 73,9 |
| 13. | $C_6H_5-\overset{O}{\underset{\|}{C}}-OCH=C\overset{CN}{\underset{COOCH_3}{\diagdown}}$<br>17,3 g<br>0,075 mol | $CH_3OH$<br>32 g<br>1 mol | HCl<br>0,9 g<br>0,025 mol | 65 | 2 | — | $CH_3O-CH=C\overset{CN}{\underset{COOCH_3}{\diagdown}}$<br>6,9 g | 65,2 |

-continued

| No. | Acyloxymethylene Compound | Alcohol | Catalyst | Temp. (°C.) | Time (h) | Work-Up | Product | Yield % |
|---|---|---|---|---|---|---|---|---|
| 14. | $CH_3-\overset{O}{\underset{\|}{C}}-O-CH=C-CN$<br>$\phantom{CH_3-C-O-CH=C}\|$<br>$\phantom{CH_3-C-O-CH=}CH_3$<br>12,5 g<br>0,1 mol | $C_2H_5OH$<br>55 g<br>1,2 mol | HCl<br>0,18 g<br>0,005 mol | 78 | 3 | — | $(C_2H_5O)_2-CH-CH-CH-CN$<br>$\phantom{(C_2H_5O)_2-CH-CH-}\|$<br>$\phantom{(C_2H_5O)_2-CH-CH-}CH_3$<br>11,9 g | 75,8 |
| 15. | $CH_3-\overset{O}{\underset{\|}{C}}-O-CH=\overset{CN}{\underset{\|}{C}}-C_6H_5$<br>14,0 g<br>0,075 mol | $C_2H_5OH$<br>46 g<br>1 mol | HCl<br>0,037 g<br>0,001 mol | 78 | 3 | — | $(C_2H_5O)_2-CH-\overset{CN}{\underset{\|}{CH}}-C_6H_5$<br>9,7 g | 58,9 |
| 16. | $CH_3-\overset{O}{\underset{\|}{C}}-O-CH=\overset{CN}{\underset{\|}{C}}-CH_2-OCH_3$<br>15,5 g<br>0,1 mol | $C_2H_5OH$<br>46 g<br>1 mol | HCl<br>0,037 g<br>0,001 mol | 78 | 3 | — | $(C_2H_5O)_2-CH-\overset{CN}{\underset{\|}{CH}}-CH_2-OCH_3$<br>13,0 g | 69,4 |

It will be understood that the specification and examples are illustrative but not limitative of the present invention and that other embodiments within the spirit and scope of the invention will suggest themselves to those skilled in the art.

What is claimed is:

1. A method for the preparation of an enol ether of the formula

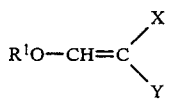
$$\text{I}$$

wherein

R$^1$ represents straight-chain or branched alkyl moieties of 1 to 20 carbon atoms or (CH$_2$)$_m$—Cyc with Cyc=isocyclic or heterocyclic, mononuclear or polynuclear aromatic or cycloaliphatic ring systems bearing in some cases substituents on the rings, with m=0 to 5, the moieties (CH$_2$)$_n$OR$^4$ or (CH$_2$—CH$_2$O)$_n$OR$^4$ with n=1 to 4 and with R$^4$=straight-chain or branched alkyl moieties of 1 to 12 carbon atoms, X represents CN or COOR$^1$ and Y represents (X being) CN, COOR$^1$, (or R$^3$ being) H, straight-chain or branched moieties of 1 to 20 carbon atoms, straight chain or branched moieties (CH$_2$)$_n$—Cn, (CH$_2$)$_n$COOR$^4$, (CH$_2$)$_n$NR$^5$$_2$, (CH$_2$)$_m$OR$^4$ or (CH$_2$)$_m$Cyc, n, m, R$^4$ and Cyc having the same meaning as above and R$^5$ alike or unalike H, straight-chain or branched alkyl moieties of 1 to 12 carbon atoms, Cyc or COR$^6$ and R$^6$=H, straight-chain or branched alkyl moieties of 1 to 12 carbon atoms or Cyc, comprising the steps of reacting an acyloxymethylene compound of the formula

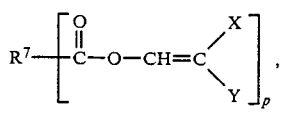
$$\text{III}$$

wherein X and Y have the meaning given above and R$^7$ represents straight-chain or branched alkyl, alkylene, alkenyl or alkenylene moieties of 1 to 12 carbon atoms, isocyclic or heterocyclic ring systems with monocyclic or polycyclic structure or (CH$_2$)$_n$Cyc, wherein n and Cyc have the meaning given above and R$^7$ represents straight-chain or branched alkyl, alkylene, alkenyl or alkenylene moieties of 1 to 12 carbon atoms, isocyclic or heterocyclic ring systems with monocyclic or polycyclic structure or (CH$_2$)$_n$Cyc, wherein n and Cyc have the meaning given above, and p=1 or 2, is reacted with an alcohol of the formula

R$^1$OH      IV, wherein R$^1$ has the meaning given above.

2. The method of claim 1, wherein the reaction takes place in the presence of a protonic or Lewis acid as a catalyst.

3. The method of claim 2 wherein 0.01 to 40 mol% catalyst is used, referred to the total mol amount of the reactants.

4. The method of claim 1 wherein 0.05 to 20 mol% catalyst is used.

5. The method of claim 1 wherein 0.01 to 40 mol% catalyst is used.

6. The method of claim 1 wherein the molar ratio of acyloxymethylene compound to alcohol is in the range of 1:1 to 1:30.

7. The method of claim 6 wherein the range is 1:2 to 1:15.

8. The method of claim 1 wherein the reaction temperature is in the range of 20° to 250° C.

9. The method of claim 1 wherein the reaction temperature is in the range of 50° to 150° C.

10. The method of claim 2 further comprising neutralizing the catalyst and separating the product from the reaction mixture.

11. A method for the preparation of an enol ether of the formula

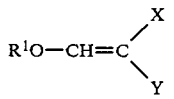
$$\text{I}$$

wherein

R$^1$ is alkyl of 1 to 4 carbon atoms, or alkyl of 2 to 3 carbon atoms and having an oxygen atom between two adjacent of the carbons;

X is CN or COOR$^1$;

Y is hydrogen, CN, COOR$^1$, R$^1$ or C$_6$H$_5$, comprising the steps of reacting an acyloxymethylene compound of the formula

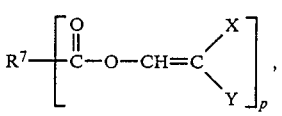
$$\text{III}$$

wherein X and Y have the meaning given above and R$^7$ is an alkyl, alkylene, alkenyl or alkenylene moieties of 1 to 4 carbon atoms, Cyc or, (CH$_2$)$_n$Cyc, wherein n is 1, 2 or 3, Cyc is C$_6$H$_5$ and p=1 or 2, with an alcohol of the formula

R$^1$OH      IV, wherein R$^1$ has the meaning given above, at a temperature in the range of 20° to 250° C., and wherein the reactants are present in a molar ratio of acyloxymethylene to alcohol of 1:1 to 1:30.

12. The method of claim 11, wherein a protonic or Lewis acid is present as a catalyst.

13. The method of claim 12, wherein 0.01 to 40 mol% of catalyst is used.

14. The method of claim 11, wherein the alcohol is selected from methanol, ethanol, propanol, isopropanol, butanol, isobutanol or sec-butanol.

15. The method of claim 11, further comprising neutralizing the catalyst and separating the product from the reaction mixture.

* * * * *